US005661158A

United States Patent [19]
Ohtsuka et al.

[11] Patent Number: 5,661,158
[45] Date of Patent: Aug. 26, 1997

[54] USE OF ANGIOTENSIN II ANTAGONISTS FOR THE TREATMENT OF HYPERLIPIDEMIA

[75] Inventors: Minoru Ohtsuka, Kobe; Shigeru Sakai, Nishinomiya, both of Japan

[73] Assignee: Fujisawa Pharmaceutical Co., Ltd., Osaka, Japan

[21] Appl. No.: 381,885

[22] PCT Filed: Jul. 27, 1993

[86] PCT No.: PCT/JP93/01052

§ 371 Date: Mar. 23, 1995

§ 102(e) Date: Mar. 23, 1995

[87] PCT Pub. No.: WO94/04153

PCT Pub. Date: Mar. 3, 1994

[30] Foreign Application Priority Data

Aug. 21, 1992 [GB] United Kingdom .................... 9217820

[51] Int. Cl.$^6$ .................... A61K 31/47; A61K 31/41
[52] U.S. Cl. .................... 514/312; 514/381; 514/824
[58] Field of Search .................... 514/312, 381, 514/824

[56] References Cited

U.S. PATENT DOCUMENTS 5,243,054  9/1993  Naka et al. .................... 548/132

OTHER PUBLICATIONS

CA 118:73665, Hill, 1992.
CA 117:245603, Darrow et al., 1992.
CA 117:131218, Bovy et al., 1992.

*Primary Examiner*—Kimberly Jordan
*Attorney, Agent, or Firm*—Oblon, Spivak, McClelland, Maier & Neustadt, P.C.

[57] ABSTRACT

A lipids-lowering agent which comprises an angiotensin II antagonist as an active ingredient.

19 Claims, No Drawings

USE OF ANGIOTENSIN II ANTAGONISTS FOR THE TREATMENT OF HYPERLIPIDEMIA

This application is a 371 of PCT/JP93/01052, filed Jul. 27, 1993.

TECHNICAL FIELD

The present invention relates to a new use of a compound having angiotensin II antagonism.

More particularly, the present invention relates to a new use of a compound having angiotensin II antagonism (hereinafter referred to as "angiotensin II antagonist") for lowering lipids in living bodies.

DISCLOSURE OF THE INVENTION

Accordingly, one object of the present invention is to provide a lipids-lowering agent which comprises an angiotensin II antagonist as an active ingredient.

Another object of the present invention is to provide a new use of an angiotensin II antagonist as a lipids-lowering agent.

Further object of the present invention is to provide a new use of an angiotensin II antagonist for manufacturing a medicament for treating or preventing lipids-associated diseases and conditions such as hypercholesterolemia, hyperlipidemia, hyperlipemia, hyperlipoproteinemia, atherosclerosis, and the like.

Still further object of the present invention is to provide a method for treating or preventing lipids-associated diseases and conditions as mentioned above which comprises administering an effective amount of an angiotensin II antagonist to a host such as animals including human.

It is reported that angiotensin II, which is a kind of hormones existing in living bodies of animals and is mainly produced by angiotensin II converting enzyme from angiotensin I, possesses strong vasoconstrictive action and releasing action for aldosterone from the adrenal cortex. Therefore, it is known that an angiotensin II antagonist exhibits vasodilating activity, and is of use for treating hypertension and some heart failures.

The inventors of the present invention extensively investigated various effects of the angiotensin II antagonists, and during such investigations, it has been found that an angiotensin II antagonist further exhibits lipids-lowering activity in living bodies of animals, particularly in blood. This finding is really new and is not expectable at all for a person skilled in this field.

In the present invention, so-called "lipids" include various cholesterols, particularly high and low density lipoprotein cholesterols (HDL-C, LDL-C), phospholipids, neutral fats (e.g. triglycerides of fatty acids, etc.), and the like. Therefore, according to the present invention, any angiotensin II antagonist is capable of lowering the level of various lipids including the above lipids in living bodies of animals, particularly total cholesterols, LDL-C and phospholipids in blood serum of human.

The angiotensin II antagonist used in the present invention is not limitative and includes any compound which exhibits angiotensin II antagonism, particularly non-peptide angiotensin II antagonist.

The preferred embodiment of the angiotensin II antagonist of the present invention can be represented by the following general formula:

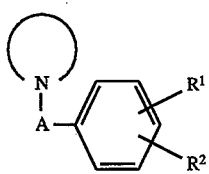

in which

R$^1$ is hydrogen, halogen, nitro, lower alkyl, lower alkoxy, amino or acylamino, R$^2$ is a group of the partial formula:

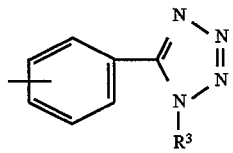

or

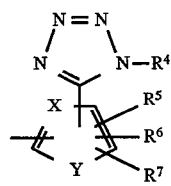

in which

R$^3$ and R$^4$ are each hydrogen or an imino-protective group,

R$^5$, R$^6$ and R$^7$ are each hydrogen, halogen, nitro, cyano, lower alkyl, lower alkenyl, lower alkylthio, mono or di or trihalo(lower)alkyl, oxo(lower)alkyl, hydroxy(lower)alkyl or optionally esterified carboxy; or R$^5$ and R$^6$ are linked together to form 1,3-butadienylene, X is N or CH, and Y is NH, O or S, A is lower alkylene, and

is condensed or uncondensed imidazolyl which may be substituted by suitable substituent(s), or a pharmaceutically acceptable salt thereof.

Another embodiment of the angiotensin II antagonist used in the present invention is a compound of the formula:

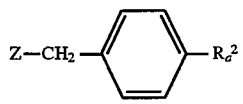

in which

Z is 2-lower alkyl-4-halo-5-hydroxy(lower)alkylimidazol-1-yl; 2-lower alkylquinolin-4-yloxy; 2-lower alkoxy-7-carboxy (or esterified carboxy)-1H-benzimidazol-1-yl; or 2- or 2,7-di or 2,5,7-tri-(lower)alkyl-3H-imidazo[4,5-b]pyridin-3-yl; and $R_a^2$ is a group of the formula:

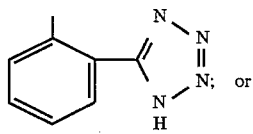

Z is 2- or 2,7-di or 2,5,7-tri-(lower)alkyl-3H-imidazo[4,5-b]pyridin-3-yl; 2-lower alkoxy-7-carboxy (or esterified carboxy) -1H-benzimidazol-1-yl; or 2-lower alkoxy- 5,7-di(lower)alkyl-3H-imidazo[4,5-b]pyridin-3-yl; and $R_a^2$ is a group of the formula:

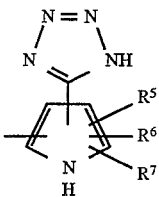

wherein $R^5$ $R^6$ and $R^7$ are each as defined above; or

Z is 2-(lower)alkyl-5-carboxy (or esterified carboxy)-4-haloimidazol-1-yl, and $R_a^2$ is combined with the adjacent benzene ring to form a group of the formula:

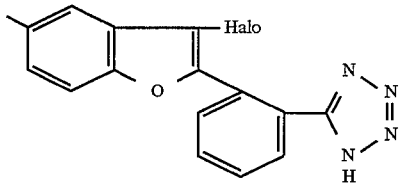

or a pharmaceutically acceptable salt thereof.

Among the compound of the formula [II], the compound of the following general formula is particularly preferable.

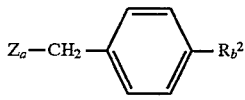

[III]

in which $Z_a$ is 2-lower alkyl-4-halo-5-hydroxy(lower)alkylimidazol-1-yl; 2-lower alkylquinolin-4-yloxy; 2-lower alkoxy-7-carboxy (or esterified carboxy)-1H-benzimidazol-1-yl; or 2- or 2,7-di or 2,5,7-tri-(lower)alkyl-3H-imidazo[4,5-b]pyridin-3-yl; and $R_b^2$ is a group of the formula:

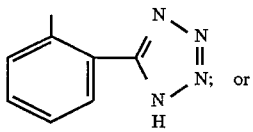

$Z_a$ is 2- or 2,7-di or 2,5,7-tri-(lower)alkyl-3H-imidazo[4,5-b]pyridin-3-yl; 2-lower alkoxy-7-carboxy (or esterified carboxy)-1H-benzimidazol-1-yl; or 2-lower alkoxy-5,7-di(lower)alkyl-3H-imidazo[4,5-b]pyridin-3-yl; and $R_b^2$ is a group of the formula:

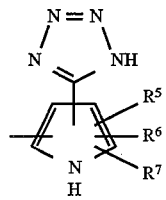

wherein $R^5$, $R^6$ and $R^7$ are each as defined above;

or a pharmaceutically acceptable salt thereof.

In the compounds of the formulae [I], [II] and [III], a suitable pharmaceutically acceptable salt of these compounds includes conventional one such as acid addition salt with an organic or inorganic acid (e.g. hydrochloride, sulfate, formate, acetate, etc.), or a salt with a base such as alkali metal salt (e.g. sodium salt, potassium salt, etc.), alkaline earth metal salt (e.g. calcium salt, etc.), organic basic salt (e.g. cyclohexylamine salt, etc.), and the like.

The most preferred embodiment of the angiotensin II antagonist used in the present invention is as follows.

2-butyl-4-chloro-5-hydroxymethyl-1-[[2'-(1H-tetrazol-5-yl)biphenyl-4-yl]methyl]imidazole or its alkali metal salt (e.g. sodium salt or potassium salt);

2-ethyl-4-[[2'-(1H-tetrazol-5-yl)biphenyl-4-yl]methoxy]quinoline or its acid addition salt (e.g. hydrochloride, etc.) or its alkali metal salt (e.g. sodium salt or potassium salt);

2-ethoxy-1-[[2'-(1H-tetrazol-5-yl)biphenyl-4-yl]methyl]-1H-benzimidazole-7-carboxylic acid or its alkali metal salt (e.g. sodium salt, disodium salt, potassium salt, etc.) or its ester [e.g. 1-(cyclohexyloxycarbonyloxy)ethyl ester, etc.];

2-butyl-3-[[2'-(1H-tetrazol-5-yl)biphenyl-4-yl]methyl]-3H-imidazo[4,5-b]pyridine or its acid addition salt (e.g. hydrochloride, etc.) or its alkali metal salt (e.g. sodium salt, potassium salt);

2-butyl-5-carboxy-4-chloro-1-[3-bromo-2-[2-(1H-tetrazol-5-yl)phenyl]benzofuran-5-ylmethyl]imidazole or its alkali metal salt (e.g. sodium salt, potassium salt);

2-propyl-7-methyl-3-[4-[2-methyl-5-(1H-tetrazol-5-yl)-pyrrol-1-yl]benzyl]-3H-imidazo[4,5-b]pyridine or its acid addition salt (e.g. hydrochloride, etc.) or its alkali metal salt (e.g. sodium salt, potassium salt);

2-ethyl-5,7-dimethyl-3-[4-[1-ethyl-5-methyl-3-(1H-tetrazol-5-yl)pyrrol-2-yl]benzyl]-3H-imidazo[4,5-b]pyridine or its acid addition salt (e.g. hydrochloride, etc.) or its alkali metal salt (e.g. sodium salt, potassium salt);

2-ethoxy-1-[4-[4-methyl-2-(1H-tetrazol-5-yl)-1-pyrrolyl]benzyl]-7-benzimidazolecarboxylic acid or its alkali metal salt (e.g. sodium salt, potassium salt, etc.) or its ester [e.g. 1-(propionyloxy)ethyl ester, etc.];

2-ethoxy-5,7-dimethyl-3-[4-[1-ethyl-5-methyl-3-(1H-tetrazol-5-yl)-pyrrolyl-2-yl]benzyl]-3H-imidazo[4,5-b]pyridine or its acid addition salt (e.g. hydrochloride, etc.) or its alkali metal salt (e.g. sodium salt, potassium salt, etc.).

The compounds of the general formulae [I], [II] and [III], and the specific compounds mentioned above are new or known compounds, and the methods for preparation thereof are described, for example, in the following publications, or they can be prepared by a conventional method.

European Patent Publication 0399731A
European Patent Publication 0399732A
European Patent Publication 0426021A
European Patent Publication 0434249A
European Patent Publication 0459136A European Patent Publication 0480204A
Japan Kokai 23868/1988
Japan Kokai 169863/1991

The suitable examples and illustrations of the various definitions used in the compounds of the formulae [I], [II] and [III] are explained in detail in the following.

The term "lower" is intended to mean 1 to 6 carbon atoms, preferably 1 to 4 carbon atoms, unless otherwise indicated.

Suitable "lower alkyl" and lower alkyl group in the term "lower alkylthio" may include straight or branched one, having 1 to 6 carbon atom(s), such as methyl, ethyl, propyl, isopropyl, butyl, t-butyl, pentyl, hexyl, preferably one having 1 to 5 carbon atoms, and the like.

Suitable "lower alkenyl" may include vinyl, 1-propenyl, allyl, 1-butenyl, 2-butenyl, 2-pentenyl, and the like, preferably one having 2 to 4 carbon atoms, in which the most preferred one is vinyl.

Suitable "lower alkylene" is one having 1 to 6 carbon atom(s) and may include methylene, ethylene, trimethylene, propylene, tetramethylene, methyltrimethylene, dimethylethylene, hexamethylene, and the like, in which the preferred one is methylene.

Suitable "halogen" and "halo" means fluoro, chloro, bromo and iodo.

Suitable "lower alkoxy" may include straight or branched one such as methoxy, ethoxy, propoxy, isopropoxy, butoxy, isobutoxy, tert-butoxy, pentyloxy, hexyloxy or the like, in which the preferable one is $C_1$-$C_4$ alkoxy.

Suitable acyl group in the term "acylamino" may include carbamoyl, thiocarbamoyl, sulfamoyl, aliphatic acyl, aromatic acyl, heterocyclic acyl, in which the preferable one is aliphatic acyl such as lower alkanoyl (e.g. formyl, acetyl, propionyl, butyryl, hexanoyl, etc.).

Suitable "mono or di or trihalo(lower)alkyl" may include chloromethyl, fluoromethyl, difluoromethyl, dichloromethyl, trifluoromethyl, trifluoromethylpropyl, and the like.

Suitable "hydroxy(lower)alkyl" may include hydroxymethyl, hydroxyethyl, and the like.

Suitable "oxo(lower)alkyl" may include formyl, formylmethyl, formylethyl, and the like.

Suitable "ester moiety" in "esterified carboxy group" may include pharmaceutically acceptable, easily removable one such as lower alkyl ester (e.g. methyl ester, ethyl estr, propyl ester, isopropyl ester, butyl ester, isobutyl ester, t-butyl ester, pentyl ester, tert-pentyl ester, hexyl ester, etc.), lower alkenyl ester (e.g. vinyl ester, allyl ester, etc.), lower alkynyl ester (e.g. ethynyl ester, propynyl ester, etc.), lower alkoxy(lower) alkyl ester (e.g. methoxymethyl ester, ethoxymethyl ester, isopropoxymethyl ester, 1-methoxyethyl ester, 1-ethoxyethyl ester, etc.), lower alkylthio(lower)alkyl ester (e.g. methylthiomethyl ester, ethylthiomethyl ester, ethylthioethyl, ester, isopropylthiomethyl ester, etc.), carboxy-substituted-lower alkyl ester (e.g. carboxymethyl ester, 2-carboxyethyl ester, 3-carboxypropyl ester, etc.), protected carboxy-substituted lower alkyl ester such as lower alkoxycarbonyl-substituted-lower alkyl ester (e.g. methoxycarbonylmehtyl ester, tert-butoxycarbonylmethyl ester, 2-tert-butoxycarbonyl-ethyl ester, 3-tert-butoxycarbonylpropyl ester, etc.), protected carboxy-substituted lower alkenyl ester such as lower alkoxycarbonyl-substituted-lower alkenyl ester 2-isobutoxycarbonyl-2-pentenyl ester, etc.), mono(or di or tri)halo(lower)alkyl ester (e.g. 2-iodoethyl ester, 2,2,2-trichloroethyl ester, etc.), lower alkanoyloxy(lower)alkyl ester [e.g. acetoxymethyl ester, propionyloxymethyl ester, butyryloxymethyl ester, valeryloxymethyl ester, pivaloyloxymehtyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.], higher alkanoyloxy(lower) alkyl ester [e.g. heptanoyloxymethyl ester, octanoyloxymethyl ester, nonanoyloxymethyl ester, decanoyloxymehtyl ester, undecanoyloxymehtyl ester, lauroyloxymethyl ester, tridecanoyloymethyl ester, myristoyloxymethyl ester, pentadecanoyloxymethyl ester, palmitoyloxymethyl ester, heptadecanoyloxymethyl ester, stearoyloxymethyl ester, nonadecanoyloxymethyl ester, eicosanoyloxymethyl ester, 1(or 2)-heptanoyloxyethyl ester, 1(or 2)-octanoyloxyethyl ester, 1(or 2)-nonanoyloxyethyl ester, 1(or 2)-decanoyloxyethyl ester, 1(or 2)-undecanoyloryethyl ester, 1(or 2)-lauroyloxyethyl ester, 1(or 2)-tridecanoyloxyethyl ester, 1(or 2)-myristoyloxyethyl ester, 1(or 2)-pentadecanoyloxyethyl ester, 1(or 2)-palmitoyloxyethyl ester, 1(or 2)-heptadecanylaxyethyl ester, 1(or 2)-stearoyloxyethyl ester, 1(or 2)-nonadecanoyl-oxyethyl ester, 1(or 2)-eicosanoyloxyethyl ester, etc.], cycloalkylcarbonyloxy(lower)alkyl ester [e.g. cyclohexylcarbonyloxymethyl ester, 1(or 2)-cyclopentylcarbonyloxyethyl ester, 1(or 2)-cyclohexylcarbonyloxyethyl ester, etc.], aroyloxy(lower) alkyl ester such as benzoyloxy(lower)alkyl ester [e.g. 1(or 2)-benzoyloxyethyl ester, etc.] heterocycliccarbonyloxy (lower)alkyl ester such as lower alkylpiperidylcarbonyloxy (lower)alkyl ester [e.g. 1(or 2)-(1-methylpiperidyl) carbonyloxyethyl, etc.], lower alalkoxycarbonyloxy(lower) alkyl ester [e.g. methoxycarbonyloxymetyl ester, propoxycarbonyloxymethyl ester, isopropoxycarbonyl-oxymethyl ester, tert-butoxycarbonyloxymethyl ester, 1(or 2)-methoxycarbonyloxyethyl ester, 1(or 2)-ethoxycarbonyloxyethyl ester, 1(or 2)-propoxycarbonyloxyethyl ester, 1(or 2)-isopropoxycarbonyloxyethyl ester, 1(or 2)-butoxycarbonyloxyethyl ester, 1(or 2)-isobutoxycarbonyloxyethyl ester, 1(or 2)-tert-butoxycarbonyloxyethyl ester, 1(or 2)-hexyloxycarbonyloxy-ethyl ester, 1(or 2 or 3)-methoxycarbonyloxypropyl ester, 1(or 2 or 3)-ethoxycarbonyloxypropyl ester, 1(or 2 or 3)-isopropoxycarbonyloxypropyl ester, 1(or 2 or 3 or 4)-ethoxycarbonyloxybutyl ester, 1(or 2 or 3 or 4)-butoxycarbonyloxybutyl ester, 1(or 2 or 3 or 4 or 5)-pentyloxycarbonyloxypentyl ester, 1(or 2 or 3 or 4 or 5)-neopentyloxycarbonyloxypentyl ester, 1(or 2 or 3 or 4 or 5 or 6) ethoxycarbonyloxyhexyl ester, etc.], cycloalkyloxycarbonyloxy(lower)alkyl ester [e.g. cyclohexyloxycarbonyloxymethyl ester, 1(or 2)-cyclopentyloxycarbonyloxyethyl ester, etc.], (5-lower alkyl-2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.], (5-lower alkyl-2-oxo-1,3-dioxolen-4-yl)(lower)alkyl ester [e.g. (5-methyl-2-oxo-1,3-dioxolen-4-yl)methyl ester, (5-tert-butyl-2-oxo-1,3-dioxolen-4-yl)methyl ester, etc.], (5-aryl-2-oxo-1,3-dioxolen-4-yl)(lower)alkyl ester such as (5-phenyl-2-oxo-1, 3-dioxolen-4-yl)(lower)alkyl ester [e.g. (5-phenyl-2-oxo-1, 3-dioxolen-4-yl)methyl ester, etc.], lower alkanesulfonyl (lower)alkyl ester (e.g. mesylmethyl ester, 2-mesylethyl ester, etc.), ar(lower)alkyl ester which may have one or more substituent(s) such as mono-(or di or tri)phenyl(lower)alkyl ester which may have one or more suitable substituent(s) (e.g. benzyl ester, 4-methoxybenzyl ester, 4-nitrobenzyl ester, phenethyl ester, benzhydryl ester, trityl ester, bis (methoxyphenyl)methyl ester, 3,4-dimethoxybenzyl ester, 4-hydroxy-3,5-di-t-butylbenzyl ester, etc.), aryl ester which may have one or more suitable substituents (e.g. phenyl ester, tolyl ester, t-butylphenyl ester, xyleyl ester, misityl ester, cumenyl ester, salicyl ester, etc.), heterocyclic ester (e.g. phthalidyl ester, 1(or 2)-phthalid-3-ylideneethyl ester, etc.), and the like.

Suitable "imino-protective group" may include conventional one, and the preferable example thereof is ar(lower) alkyl such as mono-(or di- or tri-)phenyl(lower)alkyl (e.g. benzyl, benzhydryl, trityl, etc.), acyl such as lower alkoxycarbonyl (e.g. tert-butoxycarbonyl, etc.), lower alkanesulfonyl (e.g. mesyl, etc.), arenesulfonyl (e.g. tosyl, etc.), and the like, in which the most preferred one is trityl.

The term "condensed or uncondensed imidazolyl" means 1H-imidazol-1-yl which may be condensed with aromatic or heterocyclic ring, and such group may include benzene, naphthalene, 5 or 6-membered aromatic heteromonocyclic group such as 5 or 6 membered aromatic heteromonocyclic group containing 1 to 2-nitrogen atom(s) (e.g. pyrrole, imidazole, pyrazole, pyridine, pyrimidine, etc.), 5 or 6-membered aromatic heteromonocyclic group containing 1-oxygen atom (e.g. furan, etc.), 5 or 6-membered aromatic heteromonocyclic group containing 1 sulfur atom (e.g. thiophene, etc.), and the like.

Suitable substituent in the term "condensed or uncondensed imidazolyl which may have suitable substituent(s)" is conventional one used in a pharmaceutical field and may include lower alkyl, halogen, lower alkoxy, hydroxy(lower) alkyl as mentioned above, respectively; optionally esterified carboxy such as carboxy and esterified carboxy as mentioned above; and the like.

Particularly, the preferred embodiment of

is as follows.

2-lower alkyl-3H-imidazo[4,5-b]pyridin-3-yl (e.g. 2-ethyl-3H-imidazo[4,5-b]pyridin-3-yl, 2-propyl-3H-imidazo[4,5-b]pyridin-3-yl, 2-butyl-3H-imidazo[4,5-b]pyridin-3-yl, etc.); 2,7-di(lower)alkyl-3H-imidazo[4,5-b]pyridin-3-yl (e.g. 2-ethyl-7-methyl-3H-imidazo[4,5-b]pyridin-3-yl, 7-methyl-2-propyl-3H-imidazo[4,5-b]pyridin-3-yl, 2-butyl-7-methyl-3H-imidazo[4,5-b]pyridin-3-yl etc.), 2,5,7-tri(lower)alkyl-3H-imidazo[4,5-b]pyridin-3-yl (e.g. 2-ethyl-5,7-dimethyl-3H-imidazo[4,5-b]pyridin-3-yl, 5,7-dimethyl-2-propyl-3H-imidazo[4,5-b]pyridin-3-yl, etc.); 5-halo-2-lower alkyl-3H-imidazo[4,5-b]pyridin-3-yl (e.g. 2-butyl-5-chloro-3H-imidazo[4,5-b]pyridin-3-yl, etc.), 5-lower alkoxy-2-lower alkyl-3H-imidazo[4,5-b]pyridin-3-yl (e.g. 2-butyl-5-methoxy-3H-imidazo[4,5-b]pyridin-3-yl, etc.), 6-lower alkoxycarbonyl-2-lower alkyl-1H-benzimidazol-1-yl (e.g. 2-butyl-6-ethoxycarbonyl-1H-benzimidazol-1-yl, etc.), 2-lower alkyl-3H-imidazo[4,5-d]pyrimidin-3-yl (e.g. 2-butyl-3H-imidazo[4,5-d]pyrimidin-3-yl, etc.), 2-lower alkyl-1H-thieno[3,4-d]imidazol-1-yl (e.g. 2-butyl-1H-thieno[3,4-d]imidazol-1-yl, etc.), 2-lower alkyl-4-halo-5-hydroxy(lower)alkyl-1H-imidazol-1-yl (e.g. 2-butyl-4-chloro-5-hydroxymethyl-1H-imidazol-1-yl, etc.) 2-lower alkoxy-7-lower alkanoyloxy(lower) alkoxycarbonyl-1H-benzimidazol-1-yl (e.g. 2-ethoxy-7-[1-(propionyloxy)ethoxycarbonyl]-1H-benzimidazol-1-yl, etc.), 2-lower alkoxy-5,7-di(lower)alkyl-3H-imidazo[4,5-b]pyridin-3-yl (e.g. 2-ethoxy-5,7-dimethyl-3H-imidazo[4,5-b]pyridin-3-yl, etc.) and more preferably 2-lower alkyl-3H-imidazo[4,5-b]pyridin-3-yl, 2,7-di(lower)alkyl-3H-imidazo[4,5-b]pyridin-3-yl, 2,5,7-tri(lower)alkyl-3H-imidazo[4,5-b]pyridin-3-yl, 2-lower alkoxy-7-lower alkanoyloxy(lower) alkoxycarbonyl-1H-benzimidazol-1-yl and 2-lower alkoxy-5,7-di(lower)alkyl-3H-imidazo[4,5-b]pyridin-3-yl.

For therapeutic or preventive administration, the lipids-lowering agent of the present invention are used in the form of conventional pharmaceutical preparation which contains the angiotensin II antagonist, as an active ingredient, in admixture with pharmaceutically acceptable carriers such as an organic or inorganic solid or liquid excipient which is suitable for oral, parenteral and external administration. The pharmaceutical preparation may be in solid form such as tablet, granule, powder, capsule, or liquid form such as solution, suspension, syrup, emulsion, lemonade, and the like.

If needed, there may be included in the above preparation auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the angiotensin II antagonist may vary from and also depend upon the age, conditions of the patient, a kind of diseases, a kind of the angiotensin II antagonist to be applied, and the like. In general, amounts between 0.01 mg and about 500 mg or even more per day may be administered to a patient. An average single dose of about 0.05 mg, 0.1 mg, 0.25 mg, 0.5 mg, 1 mg, 20 mg, 50 mg, 100 mg, 200 mg, or 300 mg of the angiotensin II antagonist may be used in lowering the lipids in the body.

In addition to the new lipids-lowering activity of the angiotensin II antagonist of the present invention, the compound of the general formula [II], particularly the compound of the formula [III] further exhibits suppressive effect on abnormal increase of heart, liver and kidney weights, on renal functional diseases and inflammation of arteria renalis, and on a diuretic effect. For these additional effects, the same preparation and dosage form as mentioned above are applicable.

In order to show the usefulness of the present inventions, the following examples are given.

EXAMPLE 1

Lipids-Lowering Effects on serum LDL-C and Phospholipids

[Test Method]

Male adult spontaneously hypertensive rats (SHR, 16 weeks old) were used in this test. 10 mg/kg/Day of each Test Compound was administered by incorporation into a diet for 20 weeks. Blood samples were collected from the thoracic aorta at the end of a period of drug administration, and an aliquot of serum with EDTA was provided for analysis of serum lipids.

| [Test Compound] Sodium salt of 2-butyl-3-[[2'-(1H-tetrazol-5-yl)biphenyl-4-yl]methyl]-3H-imidazo[4,5-b]pyridine [hereinafter referred to as Compound A] [Test Results] | | |
|---|---|---|
| | LDL-C (mg/dl) | Phospholipids (mg/dl) |
| Control | 33 ± 1.7 | 104 ± 2.5 |
| Compound A | 19 ± 1.1 | 90 ± 2.3 |

EXAMPLE 2

Suppressive Effect on Abnormal Increase of Heart and Liver Weights

[Test Method]

After collecting blood sample from SHR in the above Example 1, heart and liver were removed and rinsed in Tyrode's solution. Weight of each tissue was measured.

| [Test Compound] Compound A [Test Results] | | |
|---|---|---|
| | Heart Weight (mg) | Liver Weight (g) |
| Control | 1465 ± 47 | 12.73 ± 0.21 |
| Compound A | 1301 ± 17 | 11.61 ± 0.26 |

EXAMPLE 3

Suppressive Effect on Renal Functional Diseases and Inflammation of Arteria Renalis

[Test Method]

The blood sample collected from SHR in the above Example 1 was provided for analysis of blood urea nitrogen (BUN). BUN was measured by a conventional method.

Also, kidneys were removed from the tested SHR at the end of a period of drug administration and subjected to pathological analysis.

| [Test Compound] Compound A [Test Results] (1) BUN | |
|---|---|
| | BUN (mg/dl) |
| Control | 21.9 ± 1.0 |
| Compound A | 18.6 ± 0.5 |

(2) Pathological Analysis
Control: Inflammation of arteria renalis was observed.
Compound A: No inflammation of arteria renalis was observed.

EXAMPLE 4

Diuretic Effect

[Test Method]

Male adult spontaneously hypertensive rats (SHR, 16 weeks old) were used in this test. 10 Mg/kg/Day of each Test Compound was administered by incorporation into a diet for 19 weeks. Urine sample was collected for six hours after period of drug administration, and the volume of the urine was measured.

| [Test Compound] Compound A [Test Results] | |
|---|---|
| | Urine (ml/kg) |
| Control | 10.2 ± 0.98 |
| Compound A | 14.0 ± 1.16 |

As evident from the Test Results in Example 1, the angiotensin II antagonist shows strong lowering activity of lipids such as cholesterols, phospholipid, neutral fats, and the like, particularly total cholesterols, LDL-C and phospholipids, and therefore is of much use for treating and preventing lipids-associated diseases and conditions such as hypercholesterolemia, hyperlipidemia, hyperlipemia, hyperlipoproteinemia, atherosclerosis, and the like.

Further, from the Test Results in Examples 2 to 4, the angiotensin II antagonist of the compounds of the formula [II], particularly the compound of the formula [III] are considered to be of use for treating cardiac hypertrophy, renal functional diseases and nephropathy (e.g. renal insufficiency, inflammation of arteria renalis, etc.), hepatopathy (e.g. hepatic insufficiency, hepatic hypertrophy, etc.), and the like, and also of use as a diuretic.

Furthermore, it is expected that the compound of the formula [II] wherein $R^2$ is a group of the formula:

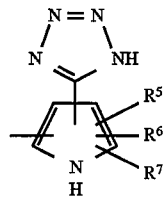

are useful for treating congestive heart failure, disorder of intracellular homeostasis, hyperuricemia, diabetic nephropathy, diabetic neuropathy, and the like.

Reference Example

To a mixture of 2-ethyl-5,7-dimethyl-3-[4-[1-ethyl-5-methyl-3-(1H-tetrazol-5-yl)pyrrol-2-yl]benzyl]-3H-imidazo-[4,5-b]pyridine (3.54 g) and ethanol (18 ml) was added 12N hydrochloric acid (0.8 ml), and the reaction mixture was heated in a boiling bath for a few minutes. The resultant solution was evaporated in vacuo, and the residue was crystallized from a mixture of 1N hydrochloric acid and ethanol to afford 2-ethyl-5,7-dimethyl-3-[4-[1-ethyl-5-methyl-3-(1H-tetrazol-5-yl)pyrrol-2-yl]benzyl]-3H-imidazo-[4,5-b]pyridine hydrochloride (2.38 g). m.p. 246°–248° C.

What is claimed is:

1. A lipid-lowering pharmaceutical composition, which comprises:

(a) an effective amount of one or more compounds of the formula:

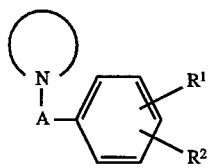

[I]

wherein
$R^1$ is hydrogen, halogen, nitro, lower alkyl, lower alkoxy, amino or acylamino,
$R^2$ is a group of the formula:

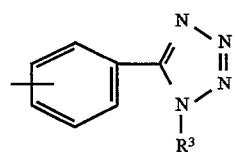

or

-continued

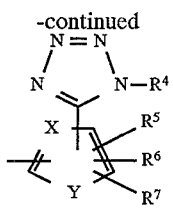

in which

R³ and R⁴ are each hydrogen or an imino-protective group;

R⁵, R⁶ and R⁷ are each hydrogen, halogen, nitro, cyano, lower alkyl, lower alkenyl, lower alkylthio, mono- or di- or trihalo(lower)alkyl, oxo(lower)alkyl, hydroxy (lower)alkyl or esterified carboxy; or R⁵ and R⁶ are linked together to form 1,3-butadienylene;

X is —N— or —CH—;

Y is —NH, —O— or —S—;

A is lower alkylene;

is uncondensed imidazolyl or imidazolyl condensed with an aromatic or heterocyclic ring selected from the group consisting of benzene, naphthalene, pyrrole, imidazolyl, pyrrazole, pyrridine, pyrimidine, furan and thiophene; wherein said condensed or uncondensed imidazolyl is unsubstituted or substituted with lower alkyl, halogen, lower alkoxy or hydroxy(lower)alkyl; or a pharmaceutically-acceptable salt thereof and (b) a pharmaceutically-acceptable carrier.

2. The lipid-lowering pharmaceutical composition of claim 1, wherein said acylamino for R¹ is lower alkanoylamino.

3. The lipid-lowering pharmaceutical composition of claim 1, wherein

is selected from the group consisting of 2-lower alkyl-3H-imidazo(4,5-b)pyridin-3-yl, 2,7-di(lower)alkyl-3H-imidazo(4,5-b)pyridin-3-yl, 2,5,7-tri(lower)alkyl-3H-imidazo(4,5-b)pyridin-3-yl, 5-halo-2-lower alkyl-3H-imidazo(4,5-b)pyridin-3-yl, 5-lower alkoxy-2-lower alkyl-3H-imidazo(4,5-b)pyridin-3-yl, 6-lower alkoxycarbonyl-2-lower alkyl-1H-benzimidazol-1-yl, 2-lower alkyl-3H-imidazo(4,5-b)pyrimidin-3-yl, 2-lower alkyl-1H-thieno(3,4-d)imidazol-1-yl, 2-lower alkyl-4-halo-5-hydroxy (lower) alkyl-1H-imidazo-1-yl, 2-lower alkoxy-7-lower alkanoyloxy(lower)alkoxycarbonyl-1H-benzimidazol-1-yl and 2-lower alkoxy-5,7-di(lower)alkyl-3H-imidazo-(4,5b)pyridin-3-yl.

4. A method of effecting a lipid-lowering effect in a mammal, which comprises administering to said mammal an effective amount of the composition of claim 1.

5. The method of claim 4, wherein said effective amount is from about 0.01 mg to 500 mg per day.

6. The lipid-lowering pharmaceutical composition of claim 1, wherein said imino-protective group is mono-, di- or triphenyl lower alkyl, lower alkoxy carbonyl or arenesulphonyl.

7. A method for treating or preventing lipid-associated diseases and conditions, which comprises administering an effective amount of the composition of claim 1 to a mammal.

8. The method of claim 7, wherein said effective amount is from about 0.01 mg to 500 mg per day.

9. The method of claim 7, wherein said lipid-associated diseases and conditions are selected from the group consisting of congestive heart failure, hyperuricemia, diabetic nephropathy and diabetic neuropathy.

10. The method of claim 9, wherein said effective amount is from about 0.01 mg to 500 mg per day.

11. A lipid-lowering pharmaceutical composition, which comprises:

(a) an effective amount of one or more compounds of the formula:

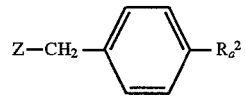

wherein

Z is 2- or 2,7-di- or 2,5,7-tri-(lower)alkyl-3H-imidazol(4,5-b)pyridine-3-yl, 2-lower alkoxy-7-carboxy-1H-benzimidazol-1-yl, 2-lower alkoxy-7-esterified carboxy-1H-benzimidazol-1-yl, or 2-lower alkoxy-5,7-di(lower)alkyl-3H-imidazol(4,5-b)pyridine-3-yl; and R_a² is a group of the formula:

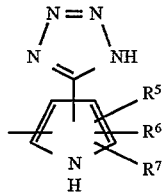

wherein

R⁵, R⁶ and R⁷ are each hydrogen, halogen, nitro, cyano, lower alkyl, lower alkenyl, lower alkylthiol, mono- or di- or tri-halo(lower)alkyl, oxo(lower)alkyl, hydroxy(lower)alkyl or esterified carboxy; or R⁵ and R⁶ are linked together to form 1,3-butadienylene; or a pharmaceutically-acceptable salt thereof; and (b) a pharmaceutically-acceptable carrier.

12. A method of effecting a lipid-lowering effect in a mammal, which comprises administering to said mammal an effective amount of the composition of claim 11.

13. The method of claim 12, wherein said effective amount is from about 0.01 mg to 500 mg per day.

14. A method for treating or preventing lipid-associated diseases and conditions, which comprises administering an effective amount of the composition of claim 11 to a mammal.

15. The method of claim 14, wherein said lipid-associated diseases and conditions are selected from the group consisting of congestive heart failure, hyperuricemia, diabetic nephropathy and diabetic neuropathy.

16. The method of claim 15, wherein said effective amount is from about 0.01 mg to 500 mg per day.

17. A lipid-lowering pharmaceutical composition, which comprises:

(a) an effective amount of one or more compounds selected from the group consisting of 2-propyl-7-methyl-3-(4-(-methyl-5-(1H-tetrazol-5-yl)-pyrrol-1-yl) benzyl)-3H-imidazol(4,5-b)pyridine, an acid addition salt thereof, an alkali metal salt thereof; 2-ethyl-5,7-dimethyl-3-(4-(1-ethyl-5-methyl-3-(1H-tetrazol-5-yl) pyrrol-2-yl)benzyl)-3H-imidazol(4,5-b)pyridine, an acid addition salt thereof, and an alkali metal salt; 2-ethoxy-1-(4-methyl)-2-(1H-tetrazol-5-yl)-1-pyrrolyl)-benzyl)-7-benzimidazole carboxylic acid, an alkali metal salt thereof, and ester thereof; and 2-ethoxy-5,7-dimethyl-3-(4-(1-ethyl-5-methyl-3-(1H-tetrazol-5-yl)-pyrrolyl-2-yl)benzyl)-3H-imidazol(4,5-b)-pyridine, an acid addition salt thereof, and an alkali metal salt thereof; and (b) a pharmaceutically-acceptable carrier.

18. A method for effecting a lipid-lowering effect in a mammal, which comprises administering to said mammal an effective amount of the composition of claim 17.

19. The method of claim 18, wherein said effective amount is from about 0.01 mg to 500 mg per day.

* * * * *

UNITED STATES PATENT AND TRADEMARK OFFICE
CERTIFICATE OF CORRECTION

PATENT NO. : 5,661,158
DATED : August 26, 1997
INVENTOR(S) : Minoru OHTSUKU, et al.

It is certified that error appears in the above-identified patent and that said Letters Patent is hereby corrected as shown below:

On the title page, item [54], and on top of column 1, the last word of the title should be:

--HYPERLIPIDAEME--

Signed and Sealed this

Twentieth Day of October, 1998

Attest:

Attesting Officer

BRUCE LEHMAN

Commissioner of Patents and Trademarks